US008374686B2

(12) United States Patent
Ghanem et al.

(10) Patent No.: US 8,374,686 B2
(45) Date of Patent: Feb. 12, 2013

(54) CONTINUOUS MONITORING OF RISK BURDEN FOR SUDDEN CARDIAC DEATH RISK STRATIFICATION

(75) Inventors: Raja N. Ghanem, Edina, MN (US); Paul J. DeGroot, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 249 days.

(21) Appl. No.: 12/793,526

(22) Filed: Jun. 3, 2010

(65) Prior Publication Data

US 2011/0137193 A1    Jun. 9, 2011

Related U.S. Application Data

(60) Provisional application No. 61/266,816, filed on Dec. 4, 2009.

(51) Int. Cl.
*A61B 5/04* (2006.01)

(52) U.S. Cl. ........................................ 600/509

(58) Field of Classification Search .......... 600/509–519
See application file for complete search history.

(56) References Cited

U.S. PATENT DOCUMENTS

| | | | | |
|---|---|---|---|---|
| 5,139,020 | A * | 8/1992 | Koestner et al. | 607/24 |
| 5,423,863 | A * | 6/1995 | Felblinger et al. | 607/5 |
| 5,560,368 | A | 10/1996 | Berger | |
| 5,987,352 | A | 11/1999 | Klein et al. | |
| 6,665,559 | B2 * | 12/2003 | Rowlandson | 600/515 |
| 6,922,585 | B2 * | 7/2005 | Zhou et al. | 600/518 |
| 6,934,577 | B2 * | 8/2005 | Hutten et al. | 600/515 |
| 6,942,622 | B1 * | 9/2005 | Turcott | 600/508 |
| 6,959,212 | B2 * | 10/2005 | Hsu et al. | 600/518 |
| 7,330,750 | B2 * | 2/2008 | Erkkila et al. | 600/509 |
| 2004/0215090 | A1 | 10/2004 | Erkkila et al. | |
| 2009/0177102 | A1 | 7/2009 | Schneider et al. | |
| 2009/0275848 | A1 | 11/2009 | Brockway et al. | |

FOREIGN PATENT DOCUMENTS

WO    2009005734 A2    1/2009

OTHER PUBLICATIONS

Nearing, Bruce D. et al., "Modified moving average analysis of T-wave alternans to predict ventricular fibrillation with high accuracy", *J. Appl Physiol* 92: 541-549, 2002.

Tereshchenko et al., abstract entitled "$T_{peak}$-$T_{end}$ Area Variability Index from Far-Field Implantable Cardioverter-Defibrillator Electrograms Predicts Sustained Ventricular Tachyarrhythmia".

Engel, et al., "Electrocardiographic Arrhymthmia Risk Testing", Current Problems in Cardiology, vol. 29, No. 7, Jul. 2004, pp. 365-432.

Lopera, et al.. "Risk Stratification for Sudden Cardiac Death: Current Approaches and Predictive Value", Current Cardiology Reviews, 2009, vol. 5, No. 1, pp. 56-64.

Rashba et al., "Enhanced Detection of Arrhythmia Vulnerability Using T Wave Alternans, Left Ventricular Ejection Fraction, and Programmed Ventricular Stimulation: A Prospective Study in Subjects with Chronic Ischemic Heart Disease", Journal of Cardiovascular Electrophysiology, vol. 15, No. 2, Feb. 2004, pp. 170-176.

(Continued)

*Primary Examiner* — Brian T Gedeon
(74) *Attorney, Agent, or Firm* — Michael C. Soldner

(57) ABSTRACT

System and method for assessing a likelihood of a patient to experience a cardiac arrhythmia. A biological sensor is configured to sense biological parameters of the patient. A processor is coupled to the biological sensor and is configured to determine the likelihood of the patient experiencing a cardiac arrhythmia based, at least in part, on a combination of the biological parameters, the combination dynamically weighting each of the plurality of biological parameters based on another one of the plurality of biological parameters.

22 Claims, 13 Drawing Sheets

OTHER PUBLICATIONS

Tonnis, et al., Grenzen und Mölichkeiten der nichtinvasiven Risikostratifikation für den plötzlichen Herztod, vol. 34, No. 7, Nov. 11, 2009, pp. 506-516.

(PCT/US2010/055407) PCT Notification of Transmittal of the International Search Report and the Written Opinion of the International Searching Authority, Mailed Jan. 28, 2011, 13 pages.

* cited by examiner

CONTINUOUS MONITORING OF RISK BURDEN FOR SUDDEN CARDIAC DEATH RISK STRATIFICATION

PRIORITY

This application claims the benefit of U.S. Provisional Application No. 61/266,816, filed on Dec. 4, 2009, entitled "Continuous Monitoring of Risk Burden for Sudden Cardiac Death Risk Stratification."

FIELD

The present invention is related to apparatus and methods for the assessment of risk of a cardiac arrhythmia and, especially to apparatus and methods for the assessment of risk of a cardiac arrhythmia by monitoring and/or measuring a biological parameter.

BACKGROUND

Cardiac pacemakers, cardioverters and defibrillators are well known in the art and provide important life-saving treatment and safeguards for many patients. Such implantable medical devices have long been utilized to treat patients prone to suffering ventricular or atrial arrhythmias such as ventricular tachycardia and ventricular fibrillation. Once implanted in the patient's body, the cardiac pacemaker, cardioverter or defibrillator monitors the patient's heart. If the heart enters fast ventricular tachycardia or ventricular fibrillation, the cardioverter/defibrillator may deliver cardioversion therapy to shock the heart out of the tachycardia or fibrillation and return the heart to normal sinus rhythm.

Determining which patients may be effectively served by the implantation of an implantable cardioverter/defibrillator may be difficult. Historically, only patients who had previously suffered ventricular fibrillation were implanted with a cardioverter/defibrillator. Subsequent clinical testing and clinical trials have provided expanded indications for patients who may benefit from a cardioverter/defibrillator. However, these indications have typically been limited to patients who had suffered a previous medical condition, such as a myocardial infarction or heart failure. As such, a substantial portion of the population which has never suffered a ventricular fibrillation episode or other traumatic cardiac event has relatively few means for being indicated for an implantable cardioverter/defibrillator.

It is known, though, that patients who have never suffered a prior cardiac episode may still experience a ventricular or atrial arrhythmia such as ventricular tachycardia or ventricular fibrillation. Research has been directed toward analyzing cardiac signals to identify characteristics indicative of an increased propensity toward suffering ventricular or atrial arrhythmia such as ventricular or atrial tachycardia, or ventricular or atrial fibrillation and sudden cardiac death. Such characteristics include, for instance, the electrophysiological properties of cardiac tissue or triggers that may tend to lead to ventricular tachycardia or ventricular fibrillation. However, the results of such research has proven only partially successful, as the results of the studies have tended to show that a particular cardiac characteristic will tend to show only one aspect of the underlying cause of a future ventricular or atrial arrhythmia such as ventricular tachyarrhythmia or ventricular fibrillation. Thus, the tests based on cardiac characteristics have tended to provide a substantially incomplete estimation of the patient's likelihood of suffering a ventricular or atrial arrhythmia such as ventricular tachycardia or ventricular fibrillation.

SUMMARY

In order to fit or equip patients who could be helped by a cardiac pacemaker, cardioverter and/or defibrillator, it would be desirable to have a more accurate indicator of which patient or patients are most at risk of ventricular or atrial arrhythmia such as fast ventricular tachycardia and/or ventricular fibrillation.

While prior techniques exist that attempt to identify patients who may be at risk of ventricular or atrial arrhythmia such as fast ventricular tachycardia and/or ventricular fibrillation, prescription of cardiac pacemaker, cardioverter and/or defibrillator resources could be greatly enhanced if procedures for risk stratification of patients at risk of ventricular or atrial arrhythmia such as fast ventricular tachycardia and/or ventricular fibrillation could be improved. For example, if it could be established with greater likelihood that a patient was at higher risk for ventricular or atrial arrhythmia such as fast ventricular tachycardia and/or ventricular fibrillation, i.e., a patient who could be helped by a cardiac pacemaker, cardioverter and/or defibrillator, then that patient could be assigned a greater likelihood of obtaining a cardiac pacemaker, cardioverter and/or defibrillator.

Perhaps of even greater benefit could be identifying patients who are at lesser risk of ventricular or atrial arrhythmias such as fast ventricular tachycardia and/or ventricular fibrillation, because then it could be established with greater confidence that patients with a lower risk of ventricular or atrial arrhythmias such as fast ventricular tachycardia and/or ventricular fibrillation do not require cardiac pacemaker, cardioverter and/or defibrillator resources saving substantial financial costs and minimizing patient discomfort due to co-morbidities related to the implantable device.

Stratifying patients at higher and lower risk of ventricular or atrial arrhythmias such as fast ventricular tachycardia and/or ventricular fibrillation can more effectively assure that patients in need of cardiac pacemaker, cardioverter and/or defibrillator therapies actually receive such therapies.

In order to conduct such a risk stratification, however, various forms of cardiac data may be required. Devices for the collection of various kinds of cardiac data, such as Holter monitors for the collection of body surface electrocardiogram data, are known in the art. However, such devices are commonly inconvenient for the patient and may carry the risk of unintended interruption in the collection of cardiac data, for instance if the monitor is jostled or if the attached electrodes separate from the patient's skin. In addition, the data collected by Holter monitors can be corrupted by the activities of daily living such as during motion. Such maneuvers may degrade the quality of the collected data. Moreover, Holter monitors and similar devices are commonly not utilized outside of a range from a few hours to a few days due to the inconvenience to the patient. As such, in circumstances where greater cardiac data may be useful, the data may either not be available, or the patient may be subjected to extended discomfort or inconvenience, and the collection of the data may be subject to undesirable interruption.

In an embodiment, a system for assessing a likelihood of a patient to experience a cardiac arrhythmia comprises a biological sensor configured to sense a plurality of biological parameters of the patient and a processor operatively coupled to the of biological sensor. The processor is configured to determine the likelihood of the patient experiencing a cardiac arrhythmia based, at least in part, on a combination of the plurality of biological parameters, the combination dynamically weighting each of the plurality of biological parameters based on another one of the plurality of biological parameters.

In an embodiment, at least one of the weightings of the plurality of biological parameters is different from at least one other one of the weightings.

In an embodiment, the processor determines the likelihood of the patient to experience a cardiac arrhythmia based, at least in part, on a quantitative analysis using a number of the plurality of biological parameters exceeding a corresponding number of predetermined thresholds.

In an embodiment, each individual one of the plurality of biological parameters corresponds to a qualitative value, and wherein the processor determines the likelihood of the patient to experience a cardiac arrhythmia based, at least in part, on a qualitative analysis using a total of the qualitative values of the plurality of biological parameters.

In an embodiment, each of the plurality of biological parameters corresponds to one of a plurality of groups, and wherein the processor is configured to determine the likelihood of the patient to experience a cardiac arrhythmia is based, at least in part on at least one biological parameter from each of the plurality of groups.

In an embodiment, one of the plurality of groups is a genetic information group.

In an embodiment, the system further comprises a user input operatively coupled to the processor and configured to receive a genetic information parameter of the genetic information group via the user input, the genetic information parameter being one of the plurality of biological parameters.

In an embodiment, the system further comprises a genetic sensor operatively coupled to the processor and configured to obtain the genetic information parameter of the genetic information group from the patient, the genetic information parameter being one of the plurality of biological parameters.

In an embodiment, one of the plurality of groups incorporates ones of the plurality of biological parameters which indicate a condition of a substrate of a heart of the patient.

In an embodiment, one of the plurality of groups incorporates ones of the plurality of biological parameters which indicate a condition of an autonomic system of the patient.

In an embodiment, one of the plurality of groups incorporates ones of the plurality of biological parameters which indicate a burden of an arrhythmia on the patient.

In an embodiment, one of the plurality of biological parameters comprises an alternating characteristic of a cardiac complex of a heart of the patient.

In an embodiment, the alternating characteristic of the cardiac complex comprises an alternating characteristic of a T-wave of the cardiac complex.

In an embodiment, the alternating characteristic of the T-wave of the cardiac complex is measured during an occurrence of an acceleration of a heart rate of the patient relative to a base heart rate of the heart after a premature ventricular contraction of the heart.

In an embodiment, the biological sensor detects one of the plurality of biological parameters being a variability of a heart rate of the patient.

In an embodiment, the patient has a heart rate at a base heart rate, and wherein one of the plurality of biological parameters comprises an acceleration of the heart rate relative to the base heart rate after a premature ventricular contraction of the heart, followed by a return to the base heart rate.

In an embodiment, one of the plurality of biological parameters comprises a characteristic of an autonomic nervous system of the patient following a decrease in a heart rate of the patient relative to a baseline heart rate.

In an embodiment, the patient has a heart having a cardiac complex comprising ventricular contractions occurring at a baseline time during the cardiac complex and wherein one of the plurality of biological parameters comprises a number of ventricular contractions occurring earlier than the baseline time over a predetermined time period.

In an embodiment, one of the plurality of biological parameters comprises a duration of a non-sustaining ventricular tachycardia.

In an embodiment, one of the plurality of biological parameters comprises a heart rate of a heart of the patient during a ventricular tachycardia.

In an embodiment, one of the plurality of biological parameters comprises an amount of time the patient experiences atrial fibrillation during a predetermined period of time.

In an embodiment, a system for assessing a likelihood of a patient to experience a cardiac arrhythmia comprises a biological sensor configured to sense a plurality of biological parameters of the patient continuously for at least fourteen days and a processor. The processor is operatively coupled to the of biological sensor and configured to determine the likelihood of the patient experiencing a cardiac arrhythmia based, at least in part, on a combination of the plurality of biological parameters, the combination individually weighting each of the plurality of biological parameters.

In an embodiment, a method for assessing a likelihood of a patient to experience a cardiac arrhythmia is conducted with an implantable device system comprising an implantable sensor and a processor. The method has the steps of sensing a plurality of biological parameters of the patient with the sensor and determining the likelihood of the patient experiencing a cardiac arrhythmia with the processor based, at least in part, on a combination of the plurality of biological parameters, the combination dynamically weighting each of the plurality of biological parameters based on another one of the plurality of biological parameters.

In an embodiment, a method for assessing a likelihood of a patient to experience a cardiac arrhythmia is conducted with an implantable device system comprising an implantable sensor and a processor. The method has the steps of sensing a plurality of biological parameters of the patient continuously for at least fourteen days with the sensor, and determining the likelihood of the patient experiencing a cardiac arrhythmia with the processor based, at least in part, on a combination of the plurality of biological parameters, the combination individually weighting each of the plurality of biological parameters.

FIGURES

DESCRIPTION

The entire content of U.S. Provisional Application Ser. No. 61/266,816, filed Dec. 4, 2009, is hereby incorporated by reference in its entirety.

Figure 1:
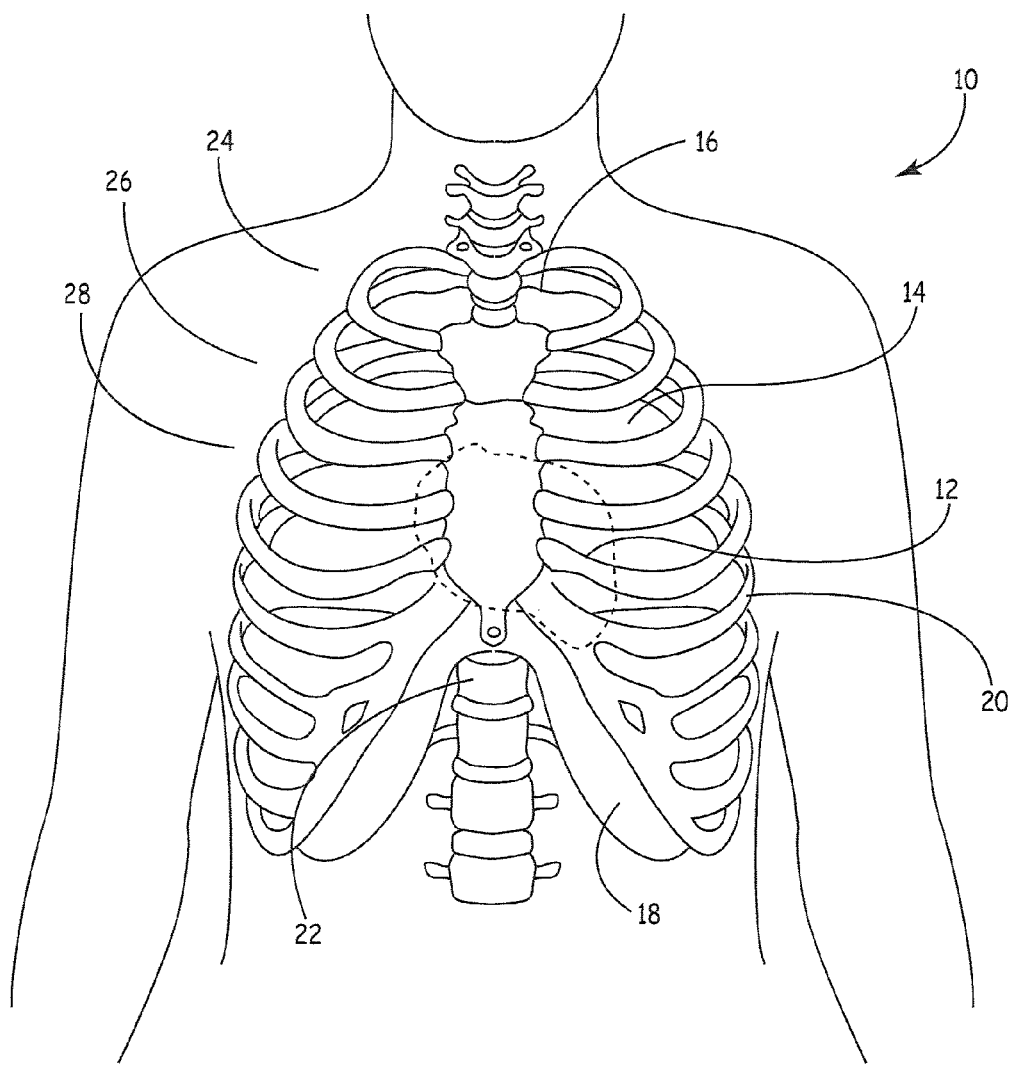
FIG. 1 is an image of a torso of a patient.

FIG. 1 is a cutaway drawing of patient 10. Heart 12 is positioned in thoracic cavity 14. Thoracic cavity 14 is commonly understood in the art to be bounded by thoracic inlet 16, diaphragm 18, ribs 20 and spine 22. Patient skin 24, musculature 26 and subcutaneous tissue 28 between skin 24 and musculature 26 are commonly not understood to be part of thoracic cavity 14.

Figure 2:
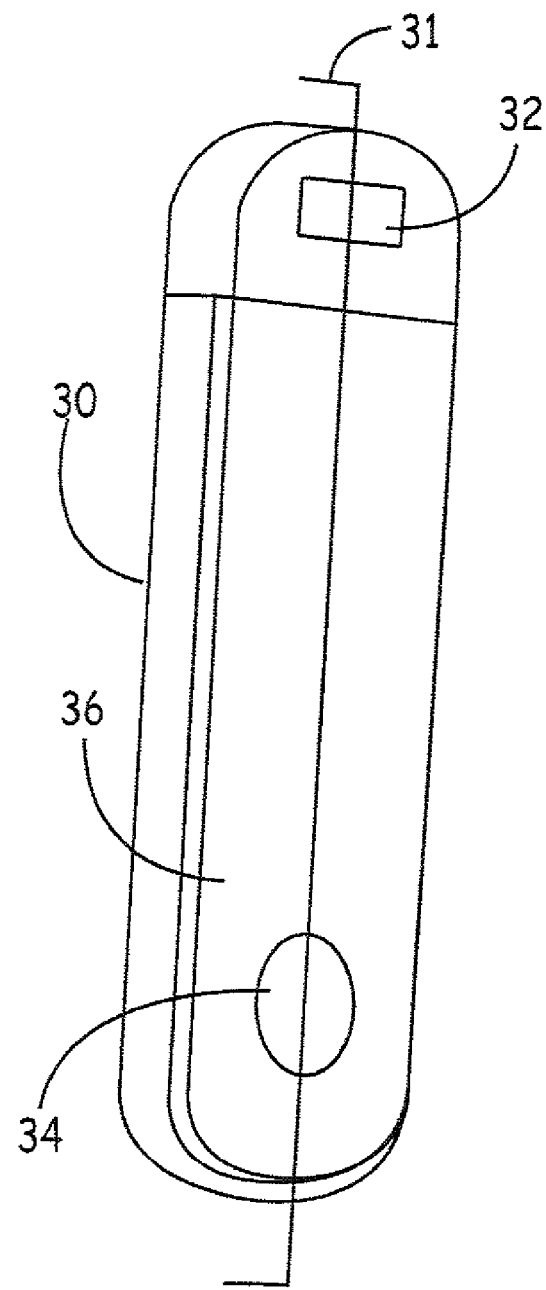
FIG. 2 is an image of an implantable device.

FIG. 2 is an image of implantable device 30. Implantable device 30 may be configured to stratify risk of heart 12 experiencing a cardiac event without meaningful risk of interruption in the collection of patient data and with greater permanence than may be provided with alternative devices, as disclosed, for instance, in U.S. Pat. No. 5,987,352, Klein et al, incorporated herein in its entirety. In various embodiments, implantable device 30 has a length along primary axis 31 from three (3) to six (6) centimeters and has a diameter less than or equal to one (1) inch (2.54 centimeters). In an embodiment, implantable device 30 has a length of approximately four (4) centimeters and a diameter orthogonal to primary axis 31 of one-half (0.5) inch (1.27 centimeters). In various embodiments, implantable device 30 is configured for subcutaneous implantation, which is known in the art to involve implantation of implantable device 30 under skin 24 but outside of thoracic cavity 14 of patient 12. In various embodiments, implantable device 30 may be implanted in tissue 28. Implantable device 30 can also be implanted sub-muscularly, that is below musculature 26, but outside of thoracic cavity 14.

Implantable device 30 may have electrodes 32, 34 at opposing ends of housing 36 along primary axis 31 of implantable device 30. In various alternative embodiments, electrodes 32, 34 are positioned on leads which extend from housing 36. In certain embodiments, the leads are similarly positioned subcutaneously. In alternative embodiments, the leads are transvenous and extend through vasculature of patient 10 and into heart 12. In various embodiments, electrodes 32, 34 are positioned a predetermined distance apart. In an embodiment, the spacing is equal to the length of implantable device 30. In alternative embodiments, electrodes 32, 34 are positioned at a distance of less than the length of implantable device 30. When implanted subcutaneously, electrodes 32, 34 may sense far-field electrical activity of heart 12 which may be interpreted in order to characterize the electrical and physical activity of heart 12.

Figure 3:
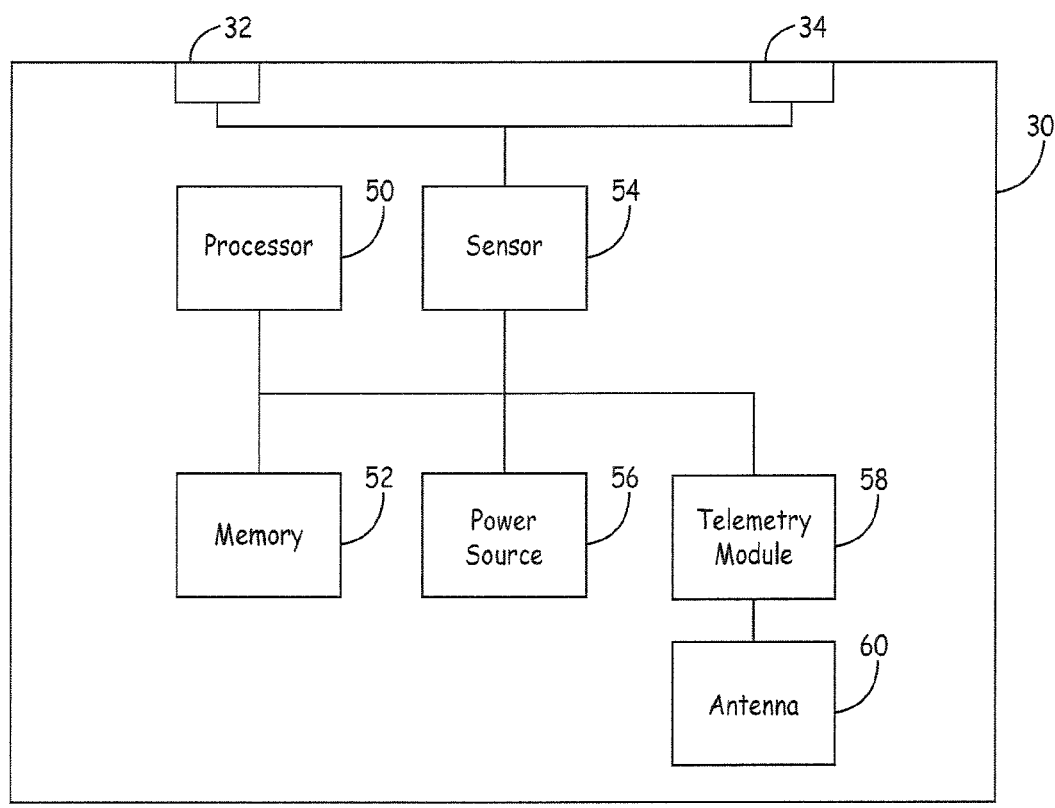
FIG. 3 is a block diagram of the implantable device of FIG. 2.

FIG. 3 is a block diagram of implantable device 30. Processor 50 provides computing and controlling functions for implantable device 30. Memory 52 stores data both stored through user input and sensed by implantable device 30 by way of electrodes 32, 34. Sensor 54 is coupled to electrodes 32, 34 and utilizes data sensed by electrodes 32, 34 to identify conditions of heart 12. In various embodiments, the function of sensor 54 is merely an aspect of the overall functionality of processor 50, and as such sensor 54 is not independent circuitry. In alternative embodiments, sensor 54 is separate componentry. Power source 56 provides power to the componentry of implantable device 30. In an embodiment, power source 56 is selected from conventional batteries well known in the implantable medical device art. In alternative embodiments, power source 56 is an alternative source of long-term power, such as a super capacitor. Telemetry module 58 is coupled to antenna 60 which, when placed in proximity of an external receiver, is configured to transmit data from processor 50, memory 52 or sensor 54 to an external device. In an embodiment, antenna 60 is an inductive coil configured to transmit data by way of an inductive field.

As cardiac signals are detected by electrodes 32, 34 and sensed by sensor 54, the data representing the cardiac signals may be stored in memory 52 and/or processed in processor 50. Alternatively, data representing the cardiac signals are transmitted the external device by way of telemetry module 58 without storage in memory 52 or processing in processor 50. In such embodiments, the external device performs the processing functions.

In order to stratify risk accurately, multiple "markers" or indicators of a cardiac condition or cardiac performance of patient 10 may be utilized together to obtain a relatively more complete evaluation of the condition of heart 12 than may be possible or practical to obtain on the basis of one measurement or marker. Taken together, multiple markers may help to obtain a risk stratification of a propensity of patient 12 toward suffering a future ventricular or atrial arrhythmia such as ventricular tachycardia or ventricular fibrillation. The risk stratification may rely not on one narrowly focused cardiac characteristic, but instead upon multiple characteristics that characterize different aspects of heart 12.

A measurement of an electrogram detected by electrodes 32, 34 positioned subcutaneously in patient 10 may generally be influenced by a relatively broad region of patient 10. Included in such broad region may be musculature 26 and the lungs of patient 10. Measurements detected with electrodes 32, 34 may be sensitive to signals generated by musculature 26 and lungs, as well as from heart 12, and are commonly referred to as far-field measurements.

In addition, measurements may be taken of non-electrical characteristics of patient 10, including, but not limited to, genetic analysis of patient 10, generally, and heart 12, specifically. Such analysis may include analysis of the patient's genes to identify mutations in heart 12, and may include analysis of the family history of patient 10 to identify increased risk of future cardiac disease.

Figure 4:
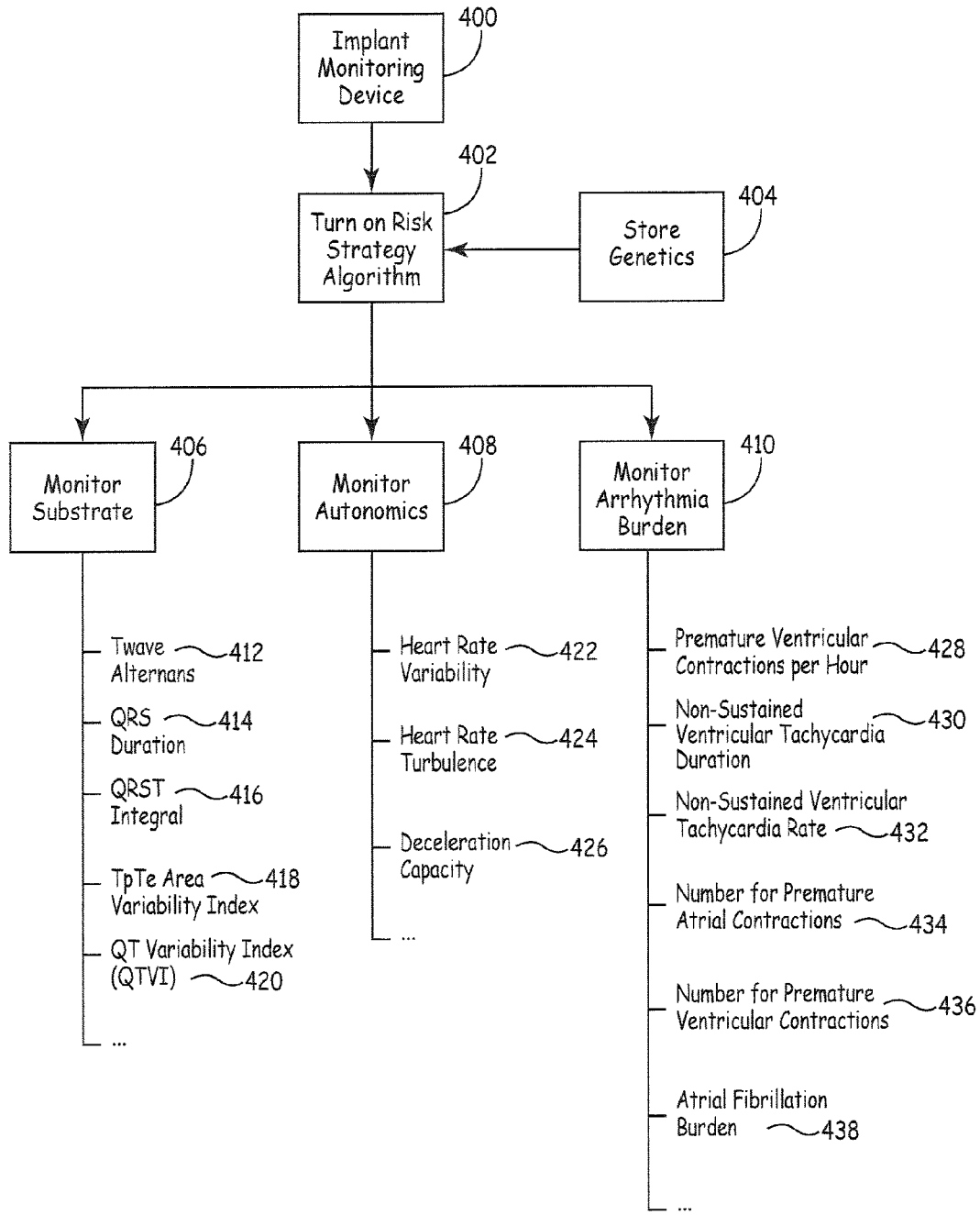
FIG. 4 is a flowchart of a method of utilizing categorized markers to assess patient risk.

FIG. 4 is a flow chart illustrating a method of utilizing implantable device 30 to obtain data useful in stratifying risk of sudden cardiac death in a patient. Implantable device 30 is implanted (400) in patient 10. A risk stratification algorithm, shown below, may be enabled (402), in an embodiment in the implantable monitoring device, in an alternative embodiment in a separate computing device. In one embodiment, genetic information may be obtained and provided to the risk stratification algorithm, in various embodiments by being stored (404) in memory module 52.

In various embodiments, cardiac data is then collected which may be utilized by the risk stratification algorithm. In an alternative embodiment, the data may be collected without first turning on (402) the risk stratification algorithm. In such an embodiment, the data may be collected and then inputted into the risk stratification algorithm after the risk stratification algorithm is turned on. The cardiac data which may be collected includes data related to a cardiac substrate of heart 12, an autonomic system of heart 12, and, in the event the patient experiences an arrhythmia of some kind, data related to the burden of the arrhythmia on patient 10 generally, referred to as the "arrhythmia burden".

Figure 5:
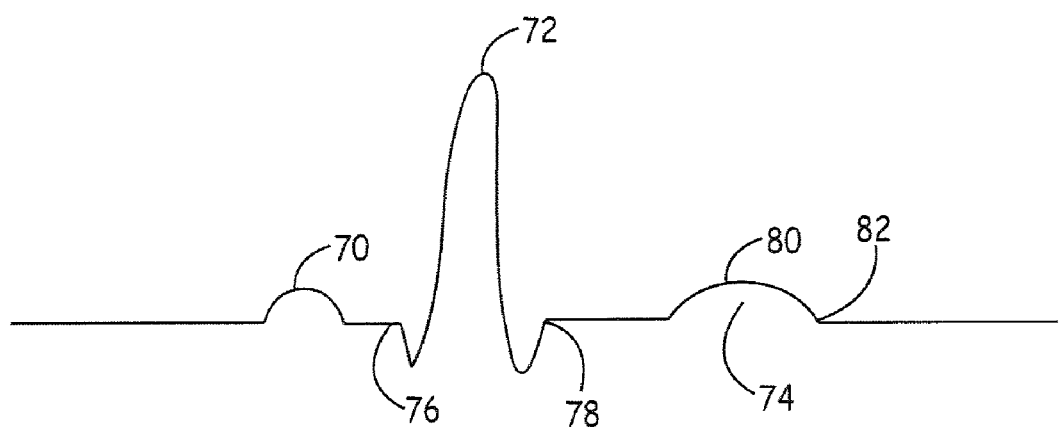
FIG. 5 is exemplary of a cardiac complex of a patient.

The substrate of heart 12 is monitored (406) for relevant data. A cardiac complex as detected as part of an electrocardiogram is illustrated in FIG. 5. P-wave 70 represents a depolarization of the atria of heart 12. QRS complex 72 represents a repolarization of the atria of heart 12 and a depolarization of the ventricles of heart 12. T-wave 74 represents the repolarization of the ventricles of heart 12. In the embodiment of implantable device 30, electrodes 32, 34 are configured to detect the electrical signal representative of the cardiac complex and sensing module 54 is configured to interpret the electrical signals sensed by electrodes 32, 34.

Figure 9:
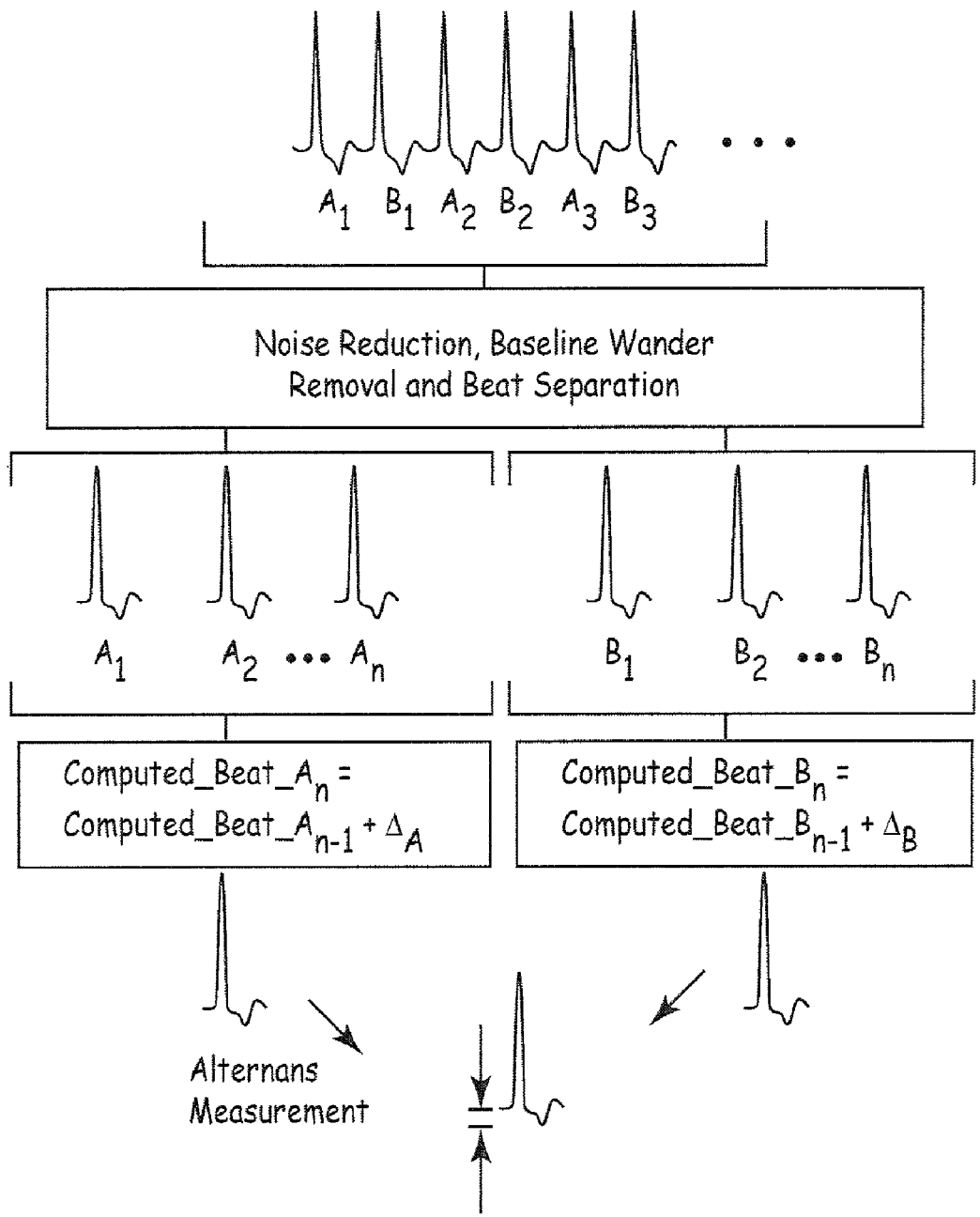
FIG. 9 is a graphical depiction of a T-wave alternans analysis using a modified moving average.
Figure 10:
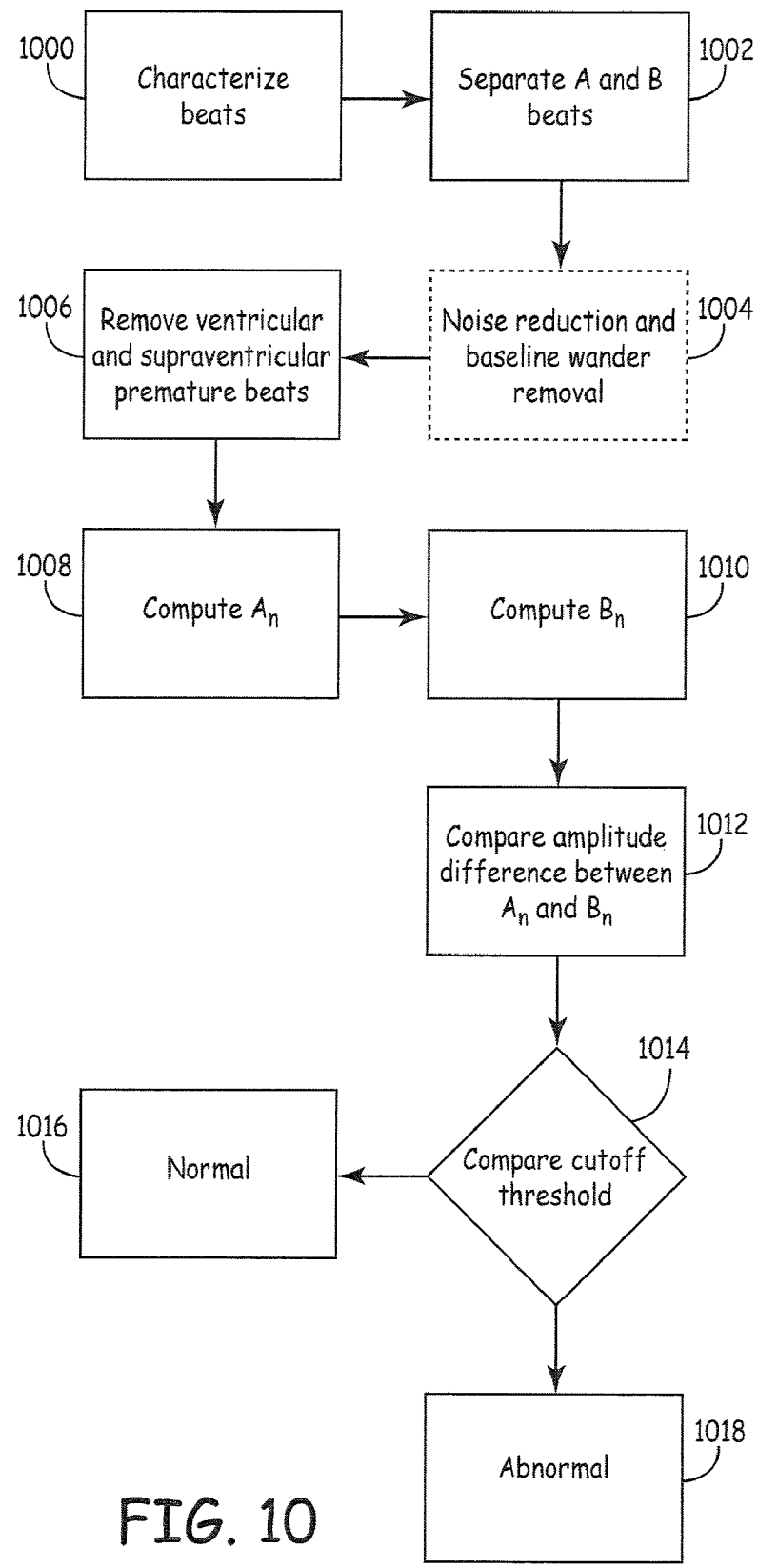
FIG. 10 is a flowchart for conducing the T-wave alternans modified moving average analysis illustrated in FIG. 9.

Examples of data related to the cardiac substrate include data related to T-wave 74 alternans (412), which accounts for beat-to-beat variability, often cyclic alternating variability, in T-waves 74 (FIGS. 9 and 10 below). Further substrate data monitored may include a duration (414) of QRS complex 72 from $QRS_{start}$ 76 to $QRS_{end}$ 78, and an integral (416) of a QRST complex, defined as the area under each of QRS complex 72 and T-wave 74.

Further, an area (418) of T-wave 74 may be computed by integrating the T-wave from $T_{peak}$ 80 to $T_{end}$ 82. Such a measurement may be indicative of a likelihood that a patient will experience fast ventricular tachycardia and/or ventricular fibrillation. A use for T-wave area (418) is described in an abstract by Larisa G. Tereshchenko et al., entitled $T_{peak}$-$T_{end}$ Area Variability Index from Far-Field Implantable Cardioverter-Defibrillator Electrograms Predicts Sustained Ventricular Tachyarrhythmia[1], incorporated here by reference in its entirety. Increased variability of $T_{peak}$-$T_{end}$ area index may provide a measure of both alternating and non-alternating repolarization instability, may predict sustained ventricular tachycardia or ventricular fibrillation events in patient 10.

[1] Tereshchenko et. al. "Tpeak-Tend Area Variability Index from Far-Field Implantable Cardioverter-Defibrillator Electrograms Predicts Sustained Ventricular Tachyarrhythmia", Heart Rhythm, vol 4, no. 5, May Supplement 2007.

Further, a variability (420) in time between $QRS_{start}$ 76 to $T_{end}$ 82 may be measured as a Q-T variability index. An example of a use for a Q-T variability index is described in U.S. Pat. No. 5,560,368, Berger, incorporated here by reference in its entirety. A template QT interval may be created based on $QRS_{start}$ 76 to $T_{end}$ for one cardiac cycle. An algorithm is then utilized to determine the QT interval of other cardiac cycles by determining how much each cycle must be stretched, i.e. elongated, or compressed in time so as to best match the template.

In an embodiment, all of the substrate data described above are utilized. In alternative embodiments, additional data related to the cardiac substrate may be incorporated. In alternative embodiments, fewer than all of the recited substrate data are utilized. In an embodiment, T-wave alternans (412) and the QRST integral (416) are utilized. In an embodiment, only T-wave alternans (412) are utilized.

Autonomics of heart 12 are likewise monitored (408). Examples of data related to autonomies, i.e., data related to the automatic nervous system, include heart rate variability (422), heart rate turbulence (424) and deceleration capacity (426). Heart rate variability (422) may be an index of variability in sequential normal heart beats. Heart beats may be identified on the basis of common points during the cardiac complex of each beat. In an embodiment, a time between consecutive beats is defined as the time between $R_{peak}$ 84 of consecutive complexes. Heart rate turbulence may reflect an immediate acceleration in heart rate followed by recovery after an occurrence of a premature ventricular contraction. Deceleration capacity may be defined as a baseline autonomic tone of patient 10 measured from the heart rate deceleration (that is, decreases in heart rate) over an extended period, typically twenty-four (24) hours. In certain embodiments, deceleration capacity may serve as a contemporary analog to heart rate variability.

In an embodiment, heart rate turbulence (424) refers to the cycle length fluctuations for a number of heart beats following a premature ventricular beat. In various embodiments, the number of beats range from five (5) beats to twenty (20) beats. In an embodiment, the number of beats is sixteen (16) beats. In sinus rhythm, the heart rate may accelerate after the premature beat and then recover to a baseline value over several beats. This adaptation of heart rate to a premature ventricular contract (PVC) may be absent in high risk patients. Mechanistically, heart rate turbulence may be due to a transient loss of vagal efferent activity due to missed baroreflex afferent input following a premature beat. A drop in blood pressure following a premature beat is sensed by a baroreflex receptor of patient 10 which then inhibits a vagal tone of patient 10, resulting in early acceleration of a cardiac cycle length. The inhibition may die out over several beats thereafter and as the blood pressure recovers to normal levels, the baroreflex receptor is reloaded and vagal activity is restored.

Heart rate turbulence is commonly derived from twenty-four hour electrocardiogram Holter recordings but may also be derived from a more continuous and longer-term monitor, such as implantable device 30 as described herein. Like heart rate variability, heart rate turbulence is computed from a plot of heart rate intervals 86 (FIG. 6a) and a heart beat number, known in the art as a tachogram. Heart rate turbulence may be characterized by two variables: turbulence onset and turbulence slope. In an embodiment, turbulence onset is defined as the difference between the mean of the first two intervals 86 consecutive complexes after the premature ventricular contraction and the mean of the last two sinus intervals 86 of consecutive complexes preceding the premature ventricular contraction divided by the mean of the last two intervals 86 between the last $R_{peak}$ 84 of consecutive complexes preceding the premature ventricular contraction. In alternative embodiments, turbulence onset may be based on individual intervals 86, or based on more than two intervals 86. In an embodiment, turbulence slope is defined as the maximum positive slope of a regression line assessed over any sequence of five (5) subsequent sinus-rhythm intervals 86 within the first fifteen (15) sinus-rhythm intervals 86 after a premature ventricular contraction. In various alternative embodiments, the possible sample set of intervals 86 after a premature ventricular contraction may be as few as two and as many as thirty, while the regression line may be based on a sequence of as few as two (2) subsequent sinus-rhythm intervals 86 and as many intervals 86 as the size of the possible sample set.

In an embodiment, if a heart rate turbulence condition is detected, an additional marker may be obtained relating to T-wave alternans. In particular, when heart 12 shows heart rate turbulence (424), T-wave alternans may be assessed according to the T-wave alternans analysis of FIGS. 9 and 10 below. Such a marker may be an additional marker relating to substrate category (406). Alternatively, such a marker may be an additional marker for autonomics category (408). Additional markers which are taken on the basis of two additional markers are contemplated. Additional markers may be obtained on the basis of timing relative to events. In an embodiment, markers may be obtained following an occurrence of a premature ventricular contraction.

Deceleration capacity (426) reflects a baseline autonomic tone and deceleration related changes in heart rate variability.

Deceleration capacity, which reflects baseline vagal autonomic tone, may be contrasted to heart rate turbulence which reflects the autonomic reflex to perturbation in cardiac function. Deceleration capacity may provide a noninvasive means to assess the deceleration related changes in heart rate thereby reflecting vagal control, and may be easier and less traumatic to accomplish than via invasive procedures.

Figure 6A:
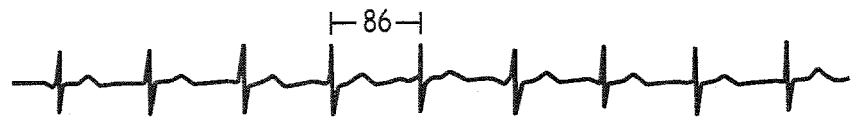
FIGS. 6a-6c are graphical depictions of an analysis of phase rectified signal averaging.
Figure 6B:
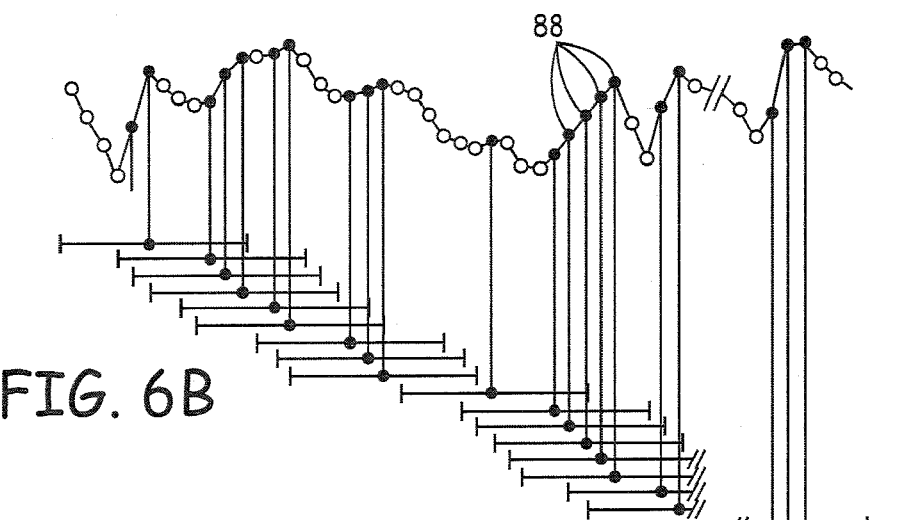
Figure 6C:
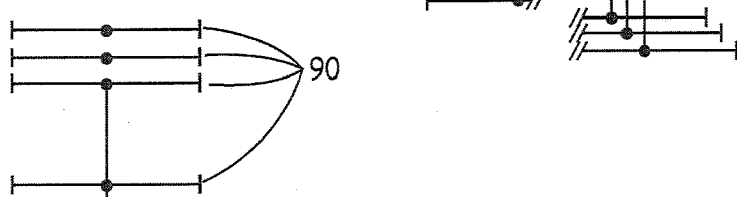
Figure 6C:
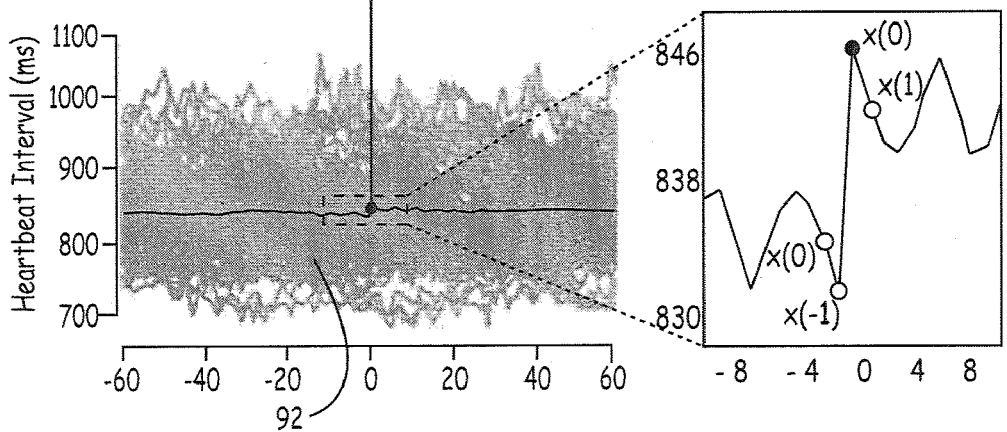
Figure 7:
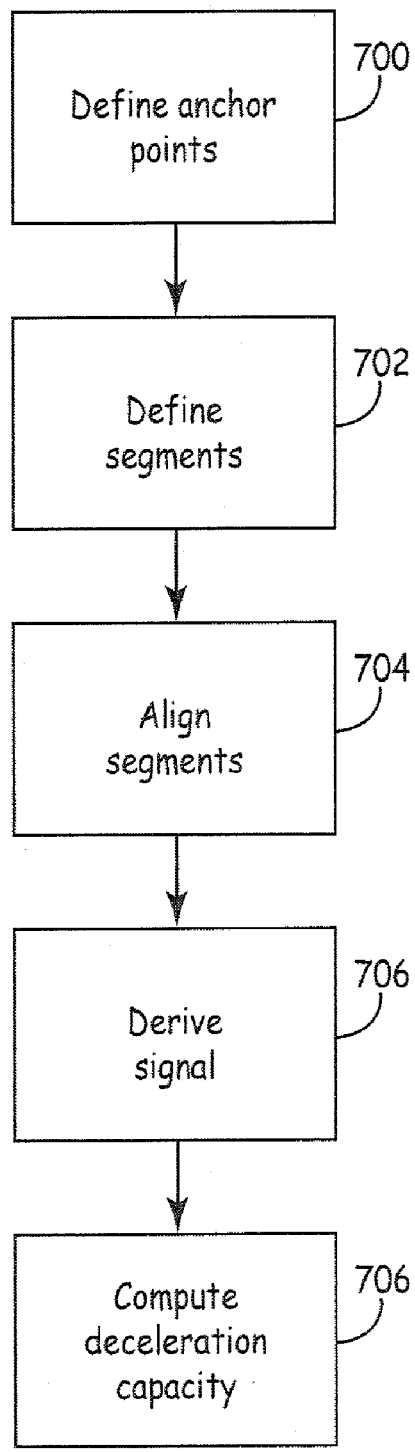
FIG. 7 is a flowchart for conducting the phase rectified signal averaging analysis illustrated in FIGS. 6a-6c.

Deceleration capacity is based on the phase rectified signal averaging (PRSA) method. The computational steps are illustrated in FIGS. 6a-6c and summarized in the flowchart of FIG. 7. Anchor points 88 are defined (700) as intervals 86 that are longer than an immediately preceding interval 86, illustrated as black circles in FIG. 6b. Next, segments 90 around anchor points 88 are defined (702). All segments have the same length and are chosen so as to resolve the lowest frequency in heart rate changes. Segments 90 are then aligned (704) around anchor points 88. Phase rectified signal averaging signal 92 is derived (706) by ensemble averaging of all of segments 90. Deceleration capacity is computed (708) according to the equation:

$$DC(AC) = [X(0) + X(1) - X(-1) - X(-2)]/4 \quad \text{Equation 1}$$

According to Equation 1, X(0) is anchor 88 about which the deceleration capacity is measured, X(1) is anchor 88 immediately following anchor 88 X(0), and X(−1) and X(−2) are anchors 88 immediately preceding anchor 88 X(0).

Examples of data related to arrhythmia burden which are monitored (426, FIG. 4) may include a number of premature ventricular contractions per hour (428), a duration and/or rate of non-sustained ventricular tachycardia (430), a non-sustained ventricular tachycardia heart rate (432), an absolute number of premature atrial contractions over a given time period (434), measurements of a frequency of premature ventricular contractions (PVC) over a given time period (436), such as a number of premature ventricular contractions per hour, and an atrial fibrillation burden (438). In general, as known in the art, atrial fibrillation burden (438) represents a frequency of occurrence of an atrial fibrillation rhythm as detected by implanted device 30 over an extended period of time. For instance, one can assess how often a patient's heart rhythm was in atrial fibrillation over a twenty-four (24) hour period, a one-to-four week period, a one-to-twelve month period, or over multiple years.

Figure 8:
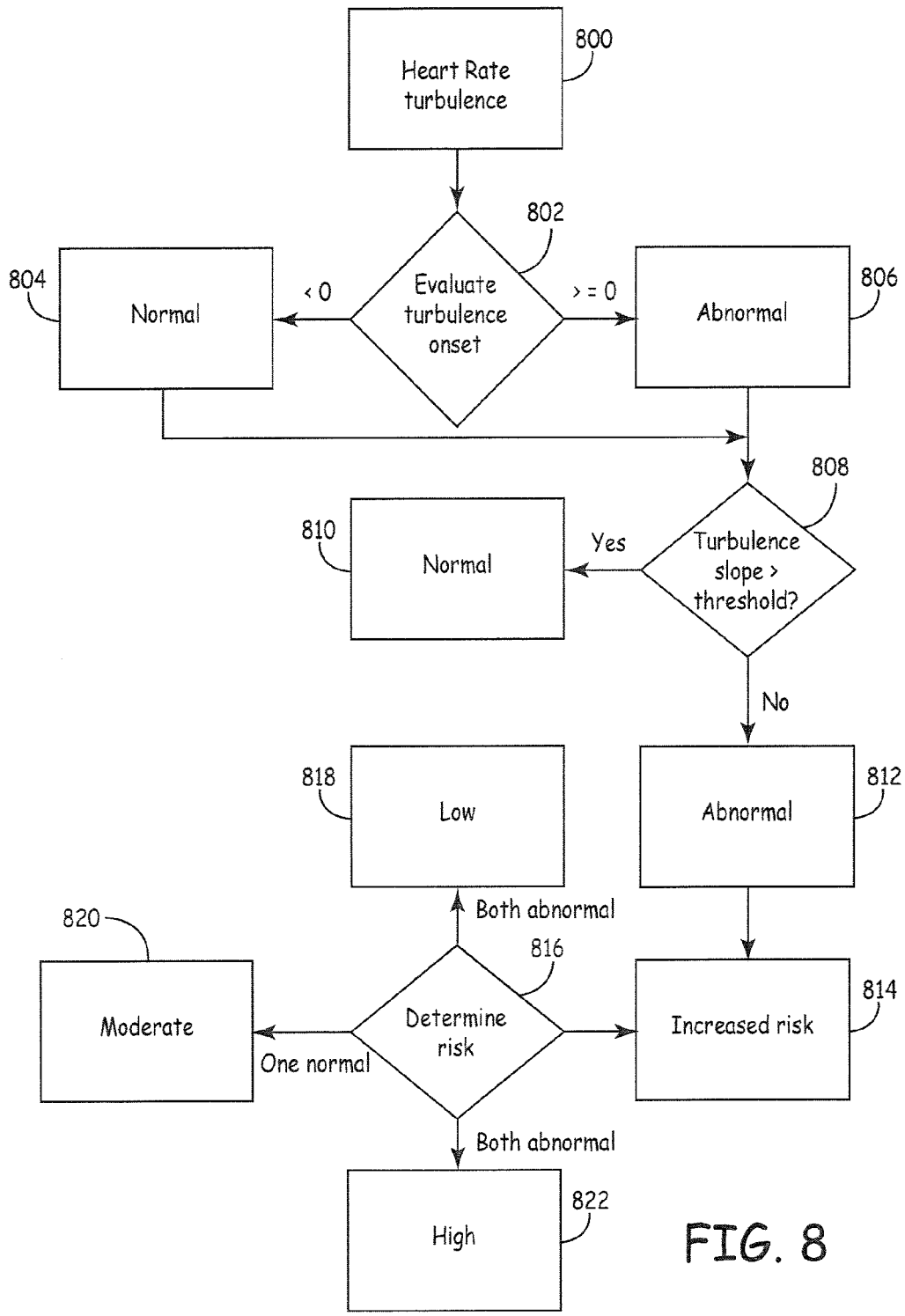
FIG. 8 is a flowchart for analyzing heart rate turbulence in a patient.

In an embodiment, after the cardiac data is collected according to FIG. 4, the risk stratification algorithm utilizes the cardiac data to obtain risk stratification. In an embodiment, illustrated in the flowchart of FIG. 8, the risk stratification algorithm factors in (800) a heart rate turbulence (422, FIG. 4) onset and evaluates (802) the turbulence onset as normal (804) if the turbulence onset is less than zero, or abnormal (806) if the turbulence onset is greater than or equal to zero, and therefore indicative of increased risk. In an embodiment, the risk stratification algorithm factors in a heart rate turbulence slope. In an embodiment, if the turbulence slope is greater than or equal to a threshold (808) of 2.5 milliseconds per interval 86, then the turbulence slope is considered normal (810). In alternative embodiments, the threshold may be less than 2.5 milliseconds to provide relatively more relaxed requirements for normalcy, and greater than 2.5 milliseconds if the requirements for normalcy may be relatively more stringent. Otherwise, the turbulence slope is considered abnormal (812) and indicative (814) of increased risk. In an embodiment, turbulence slope is the maximum slope of the regression line that fits five (5) intervals 86 during up to thirty (30) beats following a premature ventricular contraction. In alternative embodiments, the regression line may fit more or fewer intervals 86 during more or fewer beats following a premature ventricular contraction. Factoring in both turbulence onset and turbulence slope, the risk stratification algorithm may determine (816) a low risk of sudden cardiac death if both turbulence onset and turbulence slope are normal (818), a moderate risk of sudden cardiac death when either but not both are normal (820), and a high risk of sudden cardiac death if both turbulence onset and turbulence slope are abnormal (822).

In various embodiments, the risk stratification algorithm considers the T-wave alternans marker (412, FIG. 4). In some embodiments, the T-wave alternans metric utilizes the modified moving average analysis as understood in the art and as described by Nearing, Bruce D. and Verrier, Richard L., in "Modified moving average analysis of T-wave alternans to predict ventricular fibrillation with high accuracy", *J. Appl Physiol* 92: 541-549, 2002, which is incorporated herein in its entirety. FIG. 9 illustrates the modified moving average beat analysis method, which is further shown in the flowchart of FIG. 10. Heart beats are alternately characterized (1000) as A and B beats. In an embodiment, the signal is optionally subjected to noise reduction and baseline wander removal (1002), then the A and B beats are separated (1004). Ventricular and supraventricular premature beats are removed (1006). A computed $A_n$ beat is equal (1008) to the preceding computed $A_{n-1}$ plus the change in the A waves. The change is determined by a weighted difference between the current A beat and the preceding computed $A_{n-1}$. A computed $B_n$ beat is computed (1010) in the same way. The alternans measurement is obtained by comparing (1012) the difference in amplitude between the computed $A_n$ beat and the computed $B_n$ beat. In various embodiments, the number of heart beats utilized may be selectable. In an embodiment, the number of heart beats utilized may be sixteen, organized into eight consecutive A-B pairs.

In such embodiments, a cutoff threshold may be established and compared (1014) against the alternans measurement. In various embodiments, the cutoff threshold is a predetermined value. In an embodiment, the cutoff threshold is forty (40) microvolts. If the modified moving average is less than the cutoff then T-wave alternans (412) are normal (1016). If the modified moving average is greater than or equal to the cutoff then the T-wave alternans (412) are abnormal (1018).

In various embodiments, a modified moving average analysis as applied to T-wave alternans (412) above may be applied to other metrics. Application of a modified moving average may create alternate markers. In an embodiment, for instance, one alternate marker which may be utilized is to apply a modified moving average analysis to a maximum heart rate of patient 10 over each of a number of predetermined and predefined periods. For instance, in an embodiment, a maximum heart rate on each of a predetermined number of days may be subjected to modified moving average analysis according to FIG. 9.

Continuous monitoring of T-wave alternans (412) according to modified moving average analysis using minimally invasive devices, such as implantable device 10, offers the potential for (a) assessing a patient's "repolarization burden" over time, thereby circumventing the disadvantage of a single point in time monitoring, (b) tracking myocardial substrate remodeling after an index event, and (c) monitoring an effect of therapy delivered to patient 10 and, in particular, heart 12. In various embodiments, the cardiac signals generated by heart 12 may be manipulated to facilitate analysis. In an embodiment, the cardiac signal is downsampled to 256 Hertz, subjected to a bandpass filter of 0.5 Hertz-95.0 Hertz and scaled to 0.3662 µV per bit. In such an embodiment, a crescendo in T-wave alternan amplitude may be predictive of spontaneous ventricular tachycardia resulting in a relatively significant rise (p<0.05) in modified moving average values at zero to thirty (30) minutes prior to ventricular tachycardia, relative to a baseline value taken forty-five (45) to sixty (60) minutes prior to an onset of ventricular tachycardia. In other words, an increase in the modified moving average relative to a baseline may be predictive of ventricular tachycardia approximately thirty (30) to forty-five minutes after the increase begins.

In various embodiments, the risk stratification algorithm considers the number of premature ventricular contractions per hour (428). In such embodiments, the number of premature ventricular contractions per hour are compared against a cutoff threshold. In an embodiment, the cutoff threshold is ten (10) premature ventricular contractions per hour. In alternative embodiments, the cutoff threshold may be more or fewer than ten (10 premature ventricular contractions. If the number of premature ventricular contractions per hour are greater than or equal to the cutoff then the number of premature ventricular contractions are abnormal. If the number of premature ventricular contractions are less than the cutoff then the number of premature ventricular contractions are normal.

In alternative embodiments, time periods of more or less than one hour may be utilized. In an embodiment, the time periods may be selectable in increments of one minute. In such an embodiment, the cutoff threshold may be varied to compensate for the changed time period. In an embodiment, the cutoff threshold is changed proportional to the change in the time period. In various embodiments, the cutoff threshold is maintained as an integer.

In addition, as shown in FIG. 4, genetic information (404) relating to the patient and to clinical demographic information such as, but not limited to, age, ejection fraction, history of atrial fibrillation, and conduction disorders such as left bundle branch block and/or right bundle branch block may be incorporated as genetic and/or clinical data. Such data may be converted into qualitative or quantitative scores and applied like measured markers.

It is known in the art that patients with a relatively low ejection fraction may be indicated as having or being susceptible to heart failure. Factoring in the ejection fraction of the patient may impact that assessed risk the patient carries. In particular, a patient with a low ejection fraction may be indicated as being at risk of sudden cardiac death related to an onset of heart failure. In various embodiments, the risk stratification algorithm factors in whether the patient's ejection fraction is less than or equal to 35%. If the ejection fraction is less than or equal to thirty-five (35) percent, patient 10 may be evaluated as being at high risk of sudden cardiac death. If the ejection fraction is greater than thirty-five (35) percent, the patient may be at a low risk of sudden cardiac death. Additional thresholds may be utilized based on well-known standards for evaluating other cardiac risks based on ejection fraction, such as heart failure.

The above particular cases are illustrative of how data relating to risk stratification may be analyzed. Any of the factors shown in FIG. 4, as well as any other factors well known in the art, may be utilized in the risk stratification algorithm according to judgments of one skilled in the art as to what would constitute normal or abnormal states for such factors according to known standards.

While individual tests or measurements, such as those described above, may provide some indication, i.e., stratification, of risk of experiencing ventricular or atrial arrhythmias such as fast ventricular tachycardia or ventricular fibrillation, results from a plurality of markers may improve stratification for the likelihood of experiencing ventricular arrhythmias such as fast ventricular tachycardia and ventricular fibrillation. Additionally, atrial arrhythmias may similarly be detected.

In various embodiments, the results of each marker may be accorded a score indicative of the likelihood of a patient to experience ventricular or atrial arrhythmias such as fast ventricular tachycardia and/or ventricular fibrillation. Such results may be expressed either qualitatively or quantitatively.

A quantitative expression may be, for example, a numerical score accorded to the result. As an example, a numerical score greater than a predetermined threshold may be indicative of a relatively greater likelihood that the patient will experience ventricular or atrial arrhythmias such as fast ventricular tachycardia or ventricular fibrillation. Similarly, a numerical score smaller than a predetermined threshold may be indicative of a relatively lesser likelihood that the patient will experience ventricular or atrial arrhythmias such as fast ventricular tachycardia or ventricular fibrillation. In various embodiments, alternative scoring techniques may be utilized. For instance, relating to the premature ventricular contractions per hour marker (428), the actual number of premature ventricular contractions per hour may be the quantitative expression for the premature ventricular contractions per hour marker (428). Such values may then be weighted to bring the quantitative analysis in line with other markers. By contrast, in various embodiments, the quantitative evaluation for each marker may be obtained by setting multiple related thresholds for each marker and assigning a numerical value for each threshold crossed. Thus, by way of illustration, for T-wave alternans, if the modified moving average is less than 20 microvolts, a qualitative value of zero (0) may be set; if the modified moving average is greater than 20 microvolts but less than 30 microvolts, a qualitative value of one (1) may be set; if the modified moving average is greater than 30 microvolts but less than 40 microvolts a qualitative value of two (2) may be set; if the modified moving average is greater than 40 microvolts a qualitative value of three (3) may be set. Similar data may be obtained for each marker, and the qualitative values may be included in the quantitative evaluation for each category.

Quantitative values for additional markers may be selected based on similar applications to expected results and commonly known variations from typical results.

The quantitative scores from each measurement technique may be combined to obtain a quantitative or qualitative score representative of a likelihood that a patient will experience ventricular or atrial arrhythmias such as fast ventricular tachycardia or ventricular fibrillation. For example, the numerical score from each measurement may be combined by adding the scores together. In various embodiments, weighting factors may be applied to various markers to create greater emphasis on certain markers and lesser emphasis on other markers.

In an embodiment, autonomic markers may be relatively less predictive of future arrhythmia when an ejection fraction of patient 10 is less than or equal to thirty-five (35) percent. In various such embodiments, autonomic markers (408) may be assigned a relatively lower weight when the ejection fraction is less than or equal to thirty-five (35) percent. In one embodiment, autonomic markers (408) may be assigned a weight of 0.2, substrate markers (406) may be assigned a weight of 0.2, arrhythmia burden markers (410) may be assigned a weight of 0.3 and genetic markers (404) may be assigned a weight of 0.3.

In additional embodiments, patients with high ejection fractions but who have suffered from a previous acute myocardial infarction, autonomic markers (408) may have a relatively significant predictive effect. In one embodiment, autonomic markers (408) may be assigned a weight of 0.3, substrate markers (406) may be assigned a weight of 0.3, arrhythmia burden markers (410) may be assigned a weight of 0.3 and genetic markers (404) may be assigned a weight of 0.1. In an various alternative embodiments classes of markers (406), (408), (410) are not assigned weights, but rather particular markers are assigned weights. In one such embodiment, in which patient 10 has an ejection fraction of greater than thirty-five (35) percent and who had suffered a previous acute myocardial infarction, heart rate turbulence (424) has a weight of 0.3, T-wave alternans (412) has a weight of 0.3, premature ventricular contractions per hour (428) has a weight of 0.2, non-sustained ventricular tachycardia rate (436) has a weight of 0.1 and genetics (404) has a weight of 0.1.

In various embodiments, the weighting factors may be dynamic, changing based on particular circumstances of patient 10. In particular, each of markers, i.e., biological parameters, may be dynamically weighted based on another one of the markers or plurality of biological parameters of the patient. In an exemplary embodiment, heart 12 being in atrial fibrillation may cause certain markers to be weighted relatively more heavily than others. For instance, detecting atrial fibrillation may result in an increased weighting, e.g., a doubling of the effect, of QRS duration (414), QRST integral (416), number of premature atrial contractions (434) and atrial fibrillation burden (438). A detection or incorporation of a genetic mutation into genetic markers (404) which indicate a propensity for atrial fibrillation may result in a lower weight for various arrhythmia burden markers (410) relating to atrial fibrillation as it is already known that such a patient 10 is at risk of atrial fibrillation. In such circumstances, autonomic markers (408) and substrate markers (406) may be given relatively higher weights.

A detection or incorporation of a genetic marker such as a conduction disorder may result in changes in weighting of all markers of substrate group (406). In alternative embodiments, only some markers of substrate group (406) are weighted differently. In various embodiments, all markers of substrate group (406) may be altered equally. In alternative embodiments, markers of substrate group (406) may be altered variably based on an actual type of conduction disorder detected or entered. For instance, a right bundle branch block may result in a heavier weighting for QRS duration (414) and QRST integral (416) markers relative to the rest of markers of substrate group (406), though the rest of the markers of substrate group (406) may have their weighting changed. Similarly, if patient 10 suffered from left or right bundle branch block, T-wave alternans (412), QRST integral (416), QT variability index (420) and autonomies markers (408) generally may be more heavily weighted while QRS duration (414) may be less heavily weighted owing to prolonged QRS duration being expected to be experienced in a patient who has suffered right or left bundle branch block.

In alternative embodiments, quantitative scores may be developed based on multiplying the scores of individual markers together. Similarly with the quantitative scoring utilizing addition, various foul's of weighting may be applied to the individual markers.

In contrast to quantitative results, qualitative results may be expressed, not as numerical values, but rather as more granular assessments of risk. In various embodiments, the quantitative analysis may be "high" or "low", or may be "high", "middle" or "low", for example. Other qualitative expressions are also contemplated. Qualitative results from each measurement technique may be combined to obtain a qualitative score representative of an overall likelihood that a patient may experience ventricular or atrial arrhythmias such as fast ventricular tachycardia or ventricular fibrillation.

In additional embodiments, either quantitative or qualitative scores may be combined together, for instance by cross-assigning qualitative or quantitative scores, as the case may be, to respective data. For instance, a quantitative score of from "0" to "3" may correspond to a qualitative score of "low", while a qualitative score of "low" may correspond to a quantitative score of "1".

In various embodiments, other measurement techniques, other than those described herein, may be utilized that may be, at least in part, indicative of establishing a degree of risk that a patient will experience ventricular or atrial arrhythmias such as fast ventricular tachycardia or ventricular fibrillation. In various embodiments, a plurality of measurement techniques may be used or a particular number of measurement techniques in excess of two, for example, three or four, may be used or may also be used. In an embodiment, the particular measurement techniques employed may be chosen from among those available.

Figure 11:
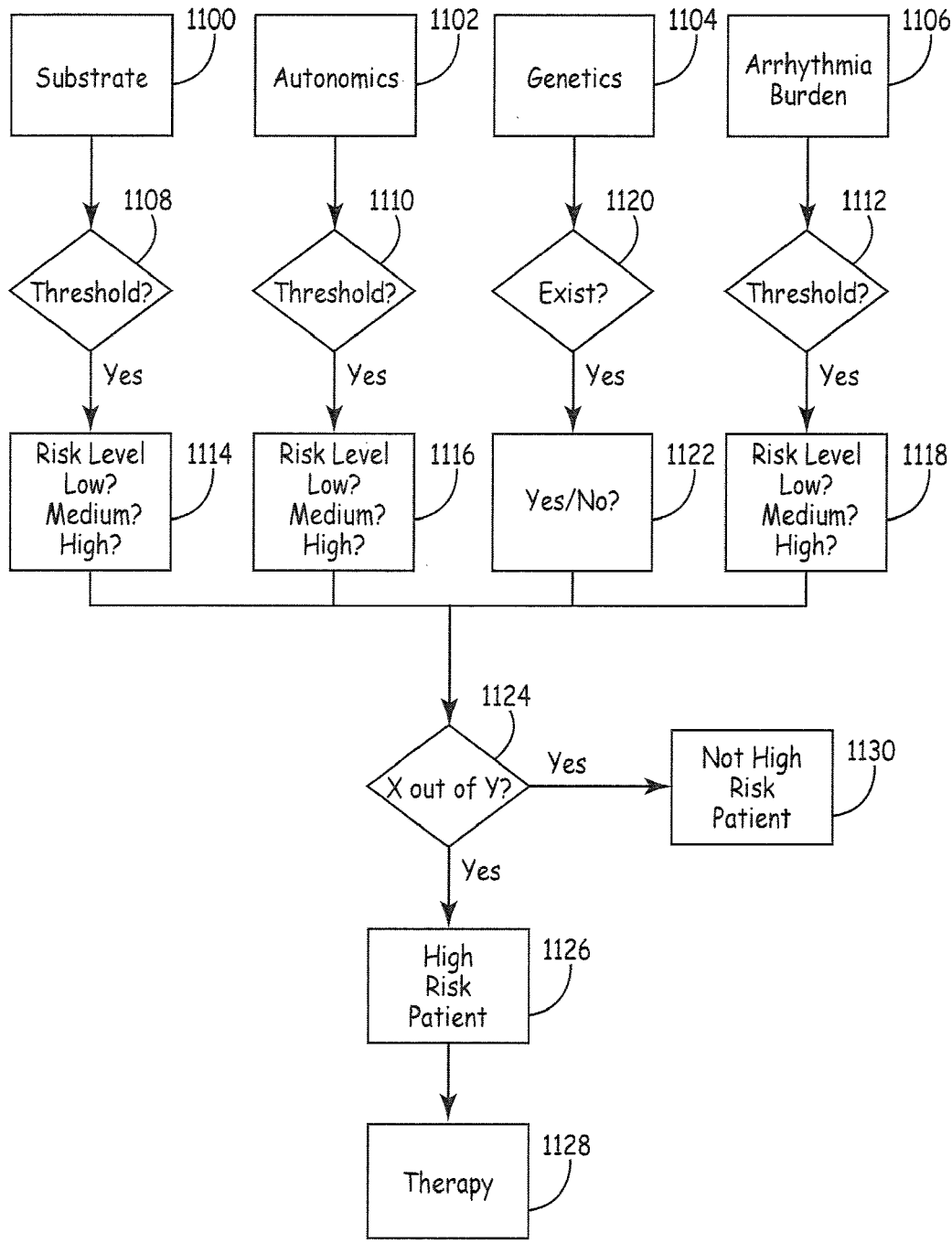
FIG. 11 is a flowchart for performing a qualitative assessment of patient risk.

FIG. 11 is a flowchart showing one embodiment of the risk stratification algorithm which utilizes qualitative assessments of each category. In it, various data related to the cardiac substrate (1100, corresponding to 406, FIG. 4), cardiac autonomics (1102, corresponding to 418, FIG. 4), genetics (1104, corresponding to 404, FIG. 4) and arrhythmia burden (1106, corresponding to 426, FIG. 4) are collected. As illustrated, data related to all of four categories are collected. In alternative embodiments, particularly where such data is not available or is not readily available, data related to only some of the categories are collected. In various embodiments, for each category for which data is provided, at least one marker is utilized. In alternative embodiments, at least two markers are utilized in at least one category. For each of the categories for which data is utilized, the data are compared (1108, 1110, 1112) against thresholds or cutoffs as described above, and individual qualitative risk assessments for each category are obtained (1114, 1116, 1118). As illustrated, the qualitative risk for each category is assessed as being "low", "medium" or "high". In the case of genetic information, an assessment may not be against a threshold or cutoff, but rather a binary assessment (1120) of whether or not a particular risk factor exists and a qualitative risk assessment obtained (1122) for genetic information. As illustrated, the qualitative risk for genetics is either "yes" or "no", according to the individual risk factors.

Once each of the categories which include data is assessed for risk factors, the individual risk factors are combined (1124) or pooled to obtain a general assessment of patient risk for sudden cardiac death. In particular, if a particular number of categories X out of the total number of categories assessed Y indicate risk of sudden cardiac death, the patient is evaluated as being at high risk (1126). As illustrated, where the categories are assessed as having "low", "medium" and "high" risk, if four categories have data, then the patient may be evaluated as being at high risk if at least two categories have high risk, or, in the case of genetics, a "yes" result, at least one category has high risk and at least two categories have medium risk, or if all four categories have medium risk. If three categories have data, then the patient may be evaluated as being at high risk if at least two categories have high risk, at least one category has medium risk and one category has high risk, or if all three categories have medium risk. Alternative relationships are contemplated. If the requirement for high risk is met, patient 10 may be treated (1128)

with therapy. If the requirements for high risk are not met (1130), no further action may be taken, or the patient may be monitored in the future.

Where each category has a risk assessment of either "low" or "high", then the number of "high" results are simply compared. In an embodiment, if at least two out of four categories show a "high" risk or, in the case of genetics a "yes" result, then the patient is assessed as having high risk of sudden cardiac death. In an embodiment where only three categories are assessed, if two out of three categories show "high" risk then the patient is assessed as having high risk of sudden cardiac death. In embodiments where two categories have data, the patient may be evaluated as being at high risk of sudden cardiac death if one category has "high" risk. Alternative relationships are contemplated.

Based on the assessment of the qualitative evaluations of each category, patient 10 may be indicated for an implantable medical device which provides therapy suitable to treat the condition to which the risk stratification algorithm indicates the patient may be susceptible. Such implantable medical devices include pacemakers and cardioverter/defibrillators, and may be further configured to treat conditions such as congestive heart failure and the like.

Figure 12:
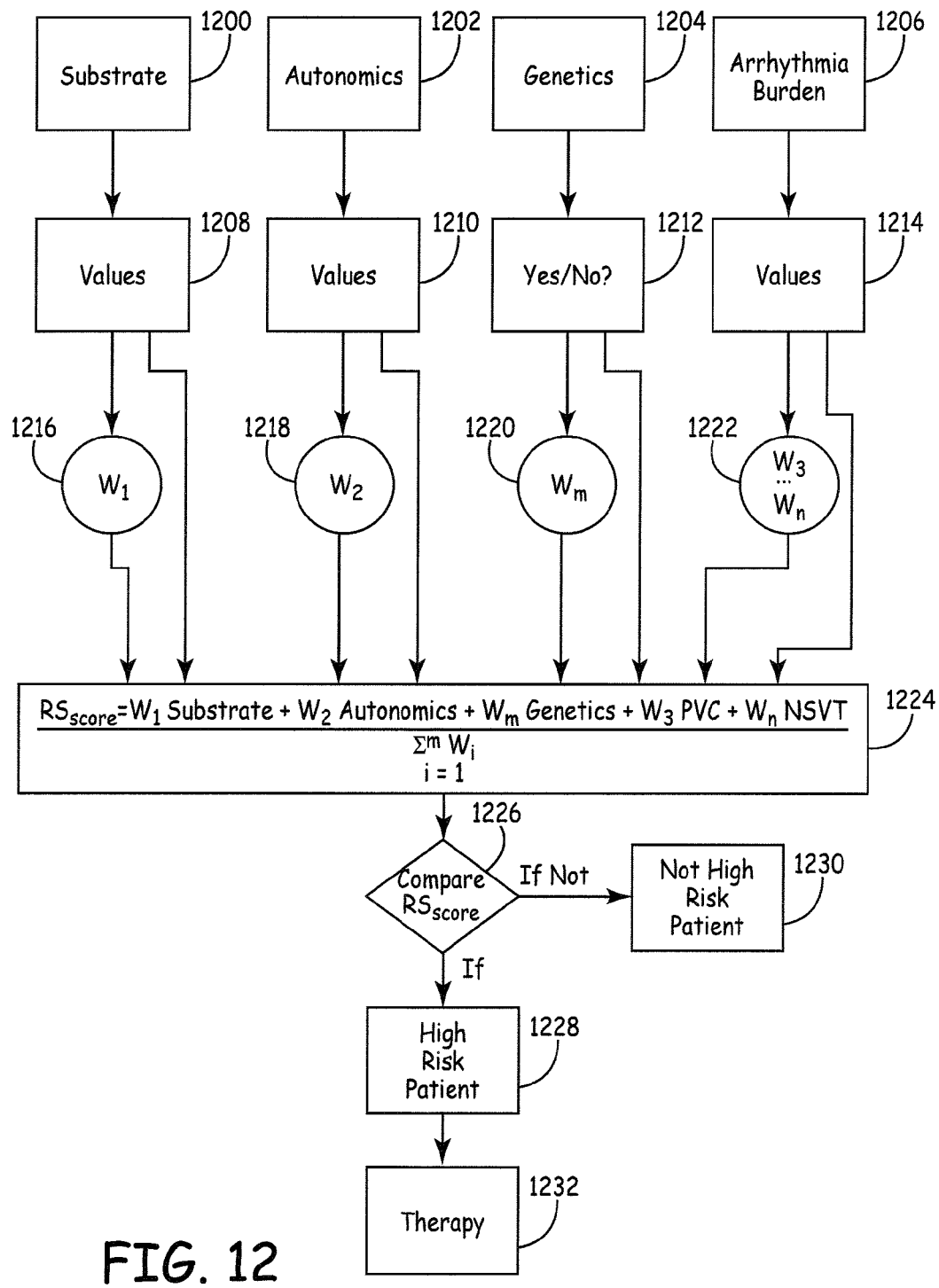
FIG. 12 is a flowchart for performing a quantitative assessment of patient risk.

FIG. 12 is a flowchart of an alternative embodiment of risk assessment algorithm which utilizes a quantitative assessment of each category. Similarly to FIG. 11, various data related to the cardiac substrate (1200, corresponding to 406, FIG. 4), cardiac autonomics (1202, corresponding to 418, FIG. 4), genetics (1204, corresponding to 404, FIG. 4) and arrhythmia burden (1206, corresponding to 426, FIG. 4) are collected. Quantitative evaluations of the data of each category are obtained (1208, 1210, 1212, 1214), and weighted (1216, 1218, 1220, 1222) for the risk stratification algorithm. As shown, each quantitative evaluation for each marker is weighted by a predefined weight W for each category with weight $W_1$ for the substrate category, $W_2$ for autonomic, $W_m$ for genetics and multiple $W_3$-$W_n$ weights for individual markers in the arrhythmia burden category. The quantitative evaluation for each category is utilized by the risk stratification algorithm to obtain (1224) a score $RS_{score}$, obtained, as illustrated, by summing all of the available quantitative marker values weighted by their corresponding weights $W_1$, $W_2$, $W_3$, $W_n$ and $W_m$ available and dividing that by the number of quantitative evaluations provided. The score $RS_{score}$ is then compared (1226) against a threshold in order to determine whether the patient is at high risk (1228) or not (1230). If patient 10 is considered to be high risk, therapy may be delivered (1232).

In various embodiments, the sum of the values of the weights is one (1). In various such embodiments, $RS_{score}$ is normalized so that it is between zero (0) and (1), and a resultant $RS_{score}$ of less than 0.25 indicates low risk, 0.25 to 0.75 indicates a moderate risk and greater than 0.75 indicates a high risk.

In an alternative embodiment, quantitative values for each marker may be utilized directly by the risk stratification algorithm without consideration within each category. In such an embodiment, the quantitative values for each marker may be summed together and divided by the total number of markers to obtain the $RS_{score}$ value. In the embodiments described, on the basis of the $RS_{score}$ the patient may be indicated for implantation of an implantable medical device as described above.

In various additional embodiments, the risk stratification algorithm may provide more than a binary assessment of risk, i.e., a quantitative risk assessment. In such embodiments, a relatively high numeric assessment of risk may indicate that the patient may benefit from the implantation of an implantable device while a very low numeric assessment of risk may indicate that the patient is in no further need of treatment or monitoring. Medium levels of assessed risk, however, may suggest that the patient is in little need of additional therapy but should be monitored. Further medium levels of assessed risk may indicate that the patient may benefit from preemptive drug therapies, but may not yet be indicated for an implantable device. Varying assessments of risk may provide varying conclusions for what treatment is provided, and such assessments and treatments may be determined on case-by-case bases.

In an embodiment relating to FIGS. 11 and 12, markers utilized include heart rate T-wave alternans (412), turbulence (424), premature ventricular contractions per hour (428) and a modified moving average of a maximum daily heart rate as described above.

Figure 13:
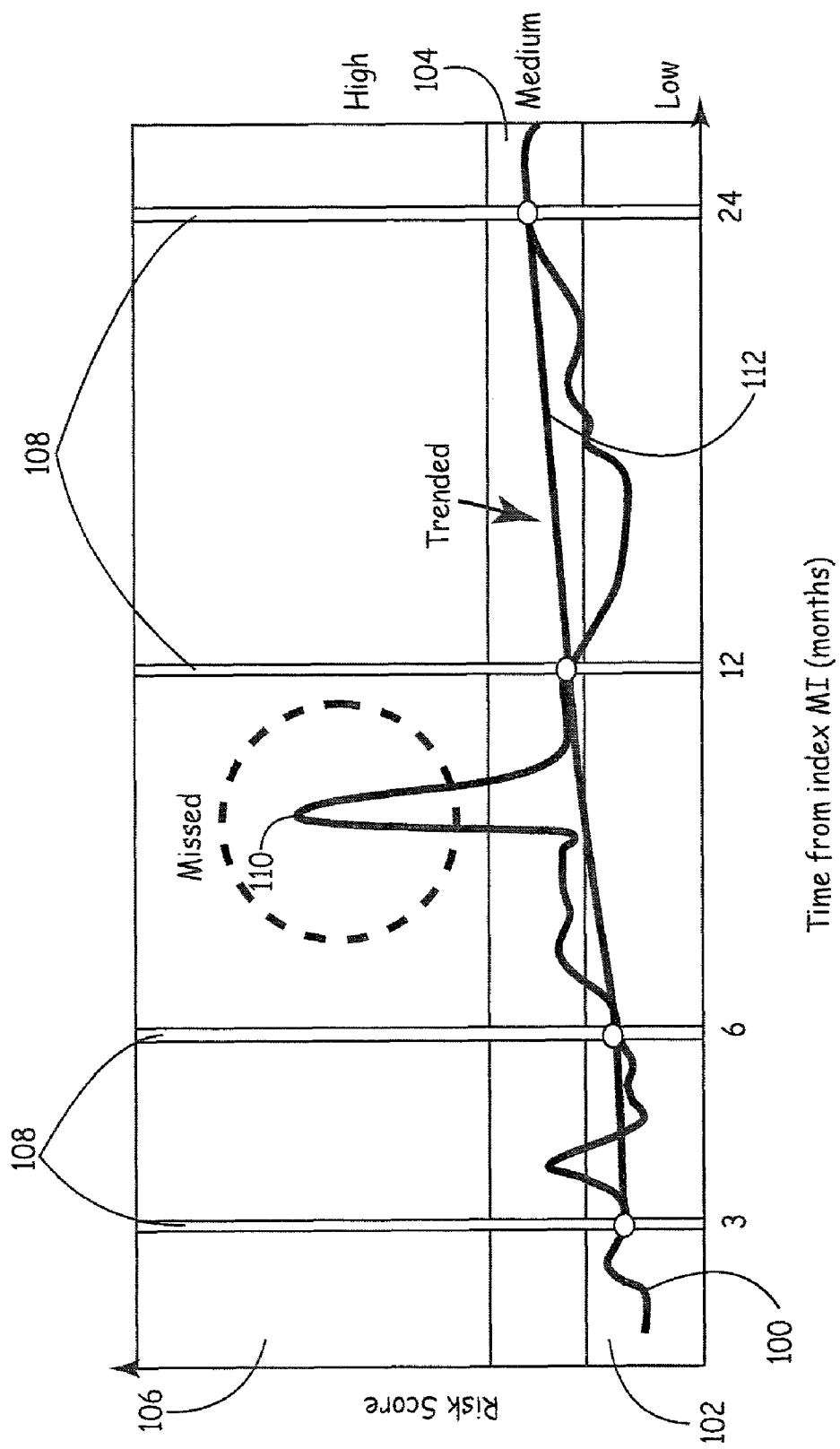
FIG. 13 is a graphical illustration of continuous monitoring by the implantable device of FIG. 2.

FIG. 13 illustrates an example of a particular utility of implantable device 30, which may monitor patient 10 continuously for as briefly as forty-eight (48) hours and more than twenty-four (24) months, in contrast with a conventional monitoring device, such as a Holter monitor, which typically monitors for a matter of hours or days. Risk line 100 represents a quantified index of risk of sudden cardiac death in patient 10 compared against horizontal bands 102, 104, 106 representing low, medium and high risk, respectively. The vertical lines 108 represent periods in which cardiac data is monitored variably by a Holter monitor and in a clinician's office. As illustrated, patient 10 experienced a spike 110 in risk line 100 which indicated a high ongoing risk of sudden cardiac death, but because the Holter monitor was not operating and because patient 10 was not being analyzed in a doctor's office, the indication was missed. Under these circumstances, the patient may have provided an indication of risk, but the indication is missed, thereby leaving an at-risk patient not-indicated for implantation with a device which could save the patient's life in the event of sudden cardiac death. By contrast, the combination of Holter monitor and clinician office visit would merely provide trend line 112 indicating a medium level of risk, well below the actual risk noted by risk line 100.

In various embodiments, analysis may occur not continually but rather at appointed times during each day of an extended period of time. In various embodiments, measurements may be obtained during predetermined time periods during a day. In an embodiment, measurement windows may be established, such as two hours. The measurement windows may be assigned during a day as determined by a medical professional. Such assignments may be on the basis of patient need. For instance, in various embodiments, a medical professional may assign windows based on a time of day at which patient 10 wakes up in the morning and eats meals. In such an embodiment, two-hour windows may be assigned from 6:00 AM to 8:00 AM, 8:00 AM to 10:00 AM, 10:00 AM to 12:00 noon and 4:00 PM to 6:00 PM. Windows may be varied in duration, number per day and timing during a day. Further, such data windows may extend for more than one day, and may be assigned on weekly, monthly or yearly bases.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for assessing a likelihood of a patient to experience a cardiac arrhythmia, comprising:

a biological sensor configured to sense a plurality of biological parameters of said patient;

a processor operatively coupled to said of biological sensor and configured to determine said likelihood of said patient experiencing a cardiac arrhythmia based, at least in part, on a combination of said plurality of biological parameters, said combination dynamically weighting each of said plurality of biological parameters based on another one of said plurality of biological parameters.

2. The system of claim 1 wherein at least one of said weightings of said plurality of biological parameters is different from at least one other one of said weightings.

3. The system of claim 1 wherein said processor determines said likelihood of said patient to experience a cardiac arrhythmia based, at least in part, on a quantitative analysis using a number of said plurality of biological parameters exceeding a corresponding number of predetermined thresholds.

4. The system of claim 1 wherein each individual one of said plurality of biological parameters corresponds to a qualitative value, and wherein said processor determines said likelihood of said patient to experience a cardiac arrhythmia based, at least in part, on a qualitative analysis using a total of said qualitative values of said plurality of biological parameters.

5. The system of claim 1 wherein each of said plurality of biological parameters corresponds to one of a plurality of groups, and wherein said processor is configured to determine said likelihood of said patient to experience a cardiac arrhythmia is based, at least in part on at least one biological parameter from each of said plurality of groups.

6. The system of claim 5 wherein one of said plurality of groups is a genetic information group.

7. The system of claim 5 wherein one of said plurality of groups incorporates ones of said plurality of biological parameters which indicate a condition of a substrate of a heart of said patient.

8. The system of claim 5 wherein one of said plurality of groups incorporates ones of said plurality of biological parameters which indicate a condition of an autonomic system of said patient.

9. The system of claim 5 wherein one of said plurality of groups incorporates ones of said plurality of biological parameters which indicate a burden of an arrhythmia on said patient.

10. The system of claim 1:
wherein each of said plurality of biological parameters corresponds to one of a plurality of groups;
wherein one of said plurality of groups incorporates ones of said plurality of biological parameters which indicate a condition of a substrate of a heart of said patient;
wherein one of said plurality of groups incorporates ones of said plurality of biological parameters which indicate a condition of an autonomic system of said patient;
wherein one of said plurality of groups incorporates ones of said plurality of biological parameters which indicate a burden of an arrhythmia on said patient; and
wherein said processor configured to determine said likelihood of said patient to experience a cardiac arrhythmia is based, at least in part on at least one biological parameter from each of said plurality of groups.

11. The system of claim 10 wherein one of said plurality of groups comprises genetic information.

12. A method for assessing a likelihood of a patient to experience a cardiac arrhythmia with an implantable device system comprising an implantable sensor and a processor, comprising the steps of:

sensing a plurality of biological parameters of said patient with said sensor;

determining said likelihood of said patient experiencing a cardiac arrhythmia with said processor based, at least in part, on a combination of said plurality of biological parameters, said combination dynamically weighting each of said plurality of biological parameters based on another one of said plurality of biological parameters.

13. The method of claim 12 wherein at least one of said weightings of said plurality of biological parameters is different from at least one other one of said weightings.

14. The method of claim 12 wherein said determining step determines said likelihood of said patient to experience a cardiac arrhythmia based, at least in part, on a quantitative analysis using a number of said plurality of biological parameters exceeding a corresponding number of predetermined thresholds.

15. The method of claim 12 wherein each individual one of said plurality of biological parameters corresponds to a qualitative value, and wherein said determining step determines said likelihood of said patient to experience a cardiac arrhythmia based, at least in part, on a qualitative analysis using a total of said qualitative values of said plurality of biological parameters.

16. The method of claim 12 wherein each of said plurality of biological parameters corresponds to one of a plurality of groups, and wherein said determining step determines said likelihood of said patient to experience a cardiac arrhythmia based, at least in part on at least one biological parameter from each of said plurality of groups.

17. The method of claim 16 wherein one of said plurality of groups is a genetic information group.

18. The method of claim 16 wherein one of said plurality of groups incorporates ones of said plurality of biological parameters which indicate a condition of a substrate of a heart of said patient.

19. The method of claim 16 wherein one of said plurality of groups incorporates ones of said plurality of biological parameters which indicate a condition of an autonomic system of said patient.

20. The method of claim 16 wherein one of said plurality of groups incorporates ones of said plurality of biological parameters which indicate a burden of an arrhythmia on said patient.

21. The method of claim 12:
wherein each of said plurality of biological parameters corresponds to one of a plurality of groups;
wherein one of said plurality of groups incorporates ones of said plurality of biological parameters which indicate a condition of a substrate of a heart of said patient;
wherein one of said plurality of groups incorporates ones of said plurality of biological parameters which indicate a condition of an autonomic system of said patient;
wherein one of said plurality of groups incorporates ones of said plurality of biological parameters which indicate a burden of an arrhythmia on said patient; and
wherein said determining step determines said likelihood of said patient to experience a cardiac arrhythmia based, at least in part on at least one biological parameter from each of said plurality of groups.

22. The method of claim 21 wherein one of said plurality of groups comprises genetic information.

* * * * *